United States Patent [19]

Hechenbleikner et al.

[11] Patent Number: 4,507,489

[45] Date of Patent: Mar. 26, 1985

[54] ACETAL ESTERS

[75] Inventors: Ingenuin Hechenbleikner, West Cornwall; William P. Enlow, Falls Village, both of Conn.

[73] Assignee: Borg-Warner Chemicals, Inc., Parkersburg, W. Va.

[21] Appl. No.: 416,538

[22] Filed: Sep. 9, 1982

Related U.S. Application Data

[63] Continuation of Ser. No. 262,266, May 11, 1981, abandoned.

[51] Int. Cl.$^3$ ............................................. C07D 319/06
[52] U.S. Cl. ...................................... 549/375; 549/374
[58] Field of Search .............................. 549/374, 375

[56] References Cited

U.S. PATENT DOCUMENTS

| | | | |
|---|---|---|---|
| 2,446,257 | 8/1948 | Barth | 549/374 |
| 2,464,430 | 3/1949 | Barth | 549/375 |
| 3,948,953 | 4/1976 | McCoy | 549/453 |
| 4,013,619 | 3/1977 | Schmidt | 549/22 |

FOREIGN PATENT DOCUMENTS

| | | | |
|---|---|---|---|
| 579179 | 7/1946 | United Kingdom | 549/375 |
| 2098213A | 11/1982 | United Kingdom | 549/374 |

*Primary Examiner*—Ethel G. Love
*Attorney, Agent, or Firm*—Robert L. Zieg

[57] ABSTRACT

Esters of monoacetals of pentaerythritol. The monoacetals result from the reaction of a 4-hydroxyphenylpropionaldehyde and pentaerythritol, and the further reaction of this monoacetal with either of two particular acid chlorides yields the esters of the invention. These esters are useful, in small proportions, to stabilize polymer compositions, especially olefin polymers.

8 Claims, No Drawings

ACETAL ESTERS

This is a continuation of application Ser. No. 262,266 filed May 11, 1981, now abandoned.

This invention relates to certain esters of monoacetals of pentaerythritol. More particularly, it relates to such esters as contain a phenolic group within their structure. It also relates to a process by which such esters may be prepared.

The esters herein are useful as polymer additives. They are especially useful in olefin polymer compositions, e.g., polypropylene compositions, where they act to impart thermal stability to such compositions. They are useful also as intermediates in the preparation of phenolic ethers which in turn are useful as plasticizers in polyester resins. Generally, olefin polymer compositions are vulnerable to deterioration of physical and chemical properties during manufacture, storage, processing and use. To overcome such deterioration, or at least to inhibit it, there have been developed additive systems which act to stabilize these polymers with respect to physical and chemical degradation caused by exposure to ordinary environmental conditions. All of these additive systems, however, while effective for their intended purpose, are characterized by one or more shortcomings.

Olefin polymers are especially susceptible to oxidative degradation. The relatively high temperatures required for their customary processing procedures such as roll milling, injection molding, extrusion and the like, invariably promote oxidation because these processes are carried out under ordinary atmospheric conditions, i.e., they are exposed to the oxygen of the atmosphere.

The significance of polymer oxidation lies in the adverse effect it has on the rheology, morphology, color, clarity, gloss and other physical properties. Impact strength may be lost; the surface may become cracked or crazed. Even a darkening of the color may provide a sufficient aesthetic disadvantage as to render the olefin polymer composition unsuitable for its intended use.

U.S. Pat. No. 3,948,946 (Hofer et al.) shows acetals of hydroxybenzaldehydes. The acetals are the reaction products of 2,2-dimethyl-1,3-propanediol, pentaerythritol, ethylene glycol, 1,2-ethanedithiol, toluene-3,4-dithiol, etc. That is, the alcohol precursor is polyhydric. The reaction of pentaerythritol, however, is carried out to completion, i.e., all of the aliphatic hydroxy groups are acetalized. The acetals are said to be effective stabilizers for organic materials.

U.S. Pat. No. 4,013,619 (Schmidt) shows acetals of certain hydroxyphenylacetaldehydes and hydroxyphenylpropionaldehydes, in some instances (see Columns 16 and 17), with pentaerythritol residues. The acetals are either monoacetals or diacetals, but the monoacetals do not contain unreacted aliphatic hydroxy groups. The acetals are said to be effective heat stabilizers in synthetic resin compositions.

U.S. Pat. No. 4,151,211 (Hechenbleikner et al.) shows acetals of 4-hydroxyphenylpropionaldehydes and such hydroxy or mercapto compounds as pentaerythritol, dodecyl mercaptan and various other acetalizing reactants, as well as their use in stabilizing polypropylene. None of the acetals, however, contain unreacted aliphatic hydroxy groups.

French Pat. No. 2,301,558 shows certain diacetals of pentaerythritol and 3,5-ditertiarybutyl-4-hydroxyphenyl propionaldehyde and 3,5-ditertiarybutylbenzaldehyde.

The invention of this application is an ester of a pentaerythritol monoacetal having the structure

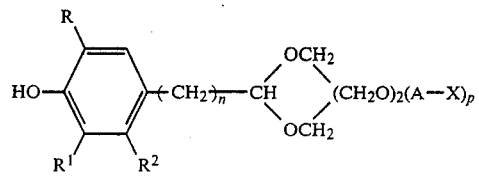

where R is alkyl, cycloalkyl or aralkyl having 3–10 carbon atoms, $R^1$ is alkyl of 1–6 carbon atoms, $R^2$ is lower alkyl or hydrogen, A is

or P—O, X is an organic radical, n is 0–3, and p is 1–2.

The invention also includes the process of preparing such esters comprising reacting a monoacetal of pentaerythritol having the structure

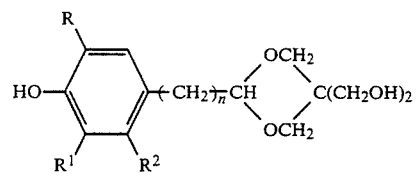

where R is alkyl, cycloalkyl or aralkyl having 3–10 carbon atoms, $R^1$ is alkyl of 1–6 carbon atoms and $R^2$ is lower alkyl or hydrogen, with an ester-forming compound having the structure $Cl_m$—A—X where m is 1 or 2, A is

or P—O, X is an organic radical and n is 0–3. The term "lower alkyl" denotes an alkyl group having 1–4 carbon atoms.

Illustrative species of R include methyl, ethyl, isopropyl, tertiarybutyl, tertiaryamyl, 2,2'-dimethylbutyl, cyclopentyl, cyclohexyl, 2-methylcyclohexyl, benzyl and phenylethyl; illustrative species of $R^1$ include methyl, ethyl, isopropyl, tertiarybutyl, tertiaryamyl and 2,2'-dimethylbutyl; illustrative species of $R^2$ include methyl, ethyl, n-propyl, isobutyl and hydrogen. Preferably, at least one of R and $R^1$ is a bulky group, e.g., tertiarybutyl or cyclohexyl.

The organic radical X is an aromatic radical, i.e., it contains a benzene ring. It may be a substituted aryl group, i.e., an alkylphenyl group (where the alkyl has 1–6 carbons) such as 4-tertiarybutylphenyl, 2,4-ditertiarybutylphenyl or 2,6-diisopropylphenyl; or a hydroxyphenyl group such as 4-hydroxy-2-methyl-3-tertiarybutylphenyl, 4-hydroxy-2,3-ditertiarybutylphenyl, 4-hydroxy-3,5-ditertiarybutylphenyl or 4-hydroxy-2-tertiarybutyl-5-n-octylphenyl. The aromatic radical may be one which is attached directly to the A group, i.e., through a benzenoid carbon atom, or it may be attached through an aliphatic carbon atoms, e.g., benzyl, 2-phenylethyl, 2-(4-hydroxyphenyl)ethyl and 2-(4-hydroxy-3,5-ditertiarybutylphenyl)ethyl.

In general, X is phenyl, alkylphenyl, or (hydroxyphenyl)alkyl, where the alkyl group(s) in each case have 1-6 carbon atoms.

The process of the invention involves reacting the above pentaerythritol acetal with the acid chloride under such conditions as to cause the evolution of hydrogen chloride. The reaction is slightly exothermic and it is accordingly advisable to employ external cooling to control the reaction. Stoichiometric quantities of the reactants should be employed for best results, i.e., two mols of carboxylic acid chloride per mol of pentaerythritol monoacetal, or one mol of the dichlorophosphite per mol of pentaerythritol monoacetal.

A hydrogen chloride acceptor is employed, usually a tertiary aliphatic amine such as triethylamine or tri-n-butylamine, i.e., one having 3–12 carbon atoms, and the reaction is best carried out in a solvent. Typical solvents include toluene, dioxane, benzene, and the like. Any inert solvent is suitable. The temperature of the reaction ordinarily is within the range of from about 10° C. to about 100° C.

The reactants, solvent and hydrogenchloride acceptor are mixed, stirred until reaction is complete and the desired solid product separated. If a pure product is desired, crystallization from a hot aliphatic hydrocarbon (such as hexane) usually will serve that purpose.

The process is illustrated by the following examples.

EXAMPLE 1

A mixture of 13.0 g. (0.034 mol) of the monoacetal of pentaerythritol and 3-(4-hydroxy-3,5-ditertiarybutylphenyl)-propionaldehyde, 17.6 g. (0.066 mol) of 4-hydroxy-3,5-ditertiarybutyl-benzoyl chloride and 115 ml. of toluene is stirred in an ice bath until the temperature is about 3° C. whereupon 11.5 ml. (8.38 g.–0.083 mol) of triethylamine is added. An exothermal reaction occurs and the temperature rises to 30° C. Stirring is continued for 45 minutes then the mixture is heated to 80° C. and filtered. The filtrate is stripped to a residue weighing 33.0 g.; it is crystallized from hot hexane to yield 11.75 g. (42.5% of the theory) of white crystals, M.P., 123°–7° C.

EXAMPLE 2

A mixture of 9.59 g. (0.025 mol) of the monoacetal of pentaerythritol and 3-(4'-hydroxy-3',5'-ditertiarybutylphenyl)propionaldehyde, 10.4 ml. (7.6 g.–0.107 mol) of triethylamine and 90 ml. of dioxane is prepared and stirred until all is in solution; a solution of 15 g. (0.051 mol) of 3-(4'-hydroxy-3',5'-ditertiarybutylphenyl)propionyl chloride is added slowly with external cooling and stirring is continued for 90 minutes at room temperature after all is added. The temperature is raised to 80° C. and held there for 90 minutes, then the mixture is filtered. The filtrate is evaporated to dryness and the residue crystallized from hot hexane to yield 16.15 g. (71% of the theory) of the desired diester, M.P., 95°–100° C.

EXAMPLE 3

To a stirred mixture of 9.5 g. (0.025 mol) of the monoacetal of pentaerythritol and 3-(4'-hydroxy-3',5'-ditertiarybutylphenyl)propionaldehyde, 10 ml. (7.3 g.–0.103 mol) of triethylamine and 100 ml. of toluene there is added, with stirring, 7.68 g. (0.025 mol) of dichloro-2,4-ditertiarybutylphenyl phosphite. An exothermic reaction ensues and the temperature of the reaction is kept below 40° C. by means of an ice bath. When the reaction has subsided the product mixture is filtered and the filtrate is evaporated to 15.0 g. of a yellow, gummy residue. Crystallization from hot heptane yields 12.5 g. (81% of the theory) of a light yellow solid, M.P., 138°–140° C.

EXAMPLE 4

The procedure of Example 2 is repeated except that the monoacetal reactant is derived from 3-(2',3'-dimethyl-5'-tertiarybutylphenyl)propionaldehyde.

EXAMPLE 5

The procedure of Example 3 is repeated except that the phosphite reactant is dichloro-2,6-ditertiarybutylphenyl phosphite.

The acetal esters of the invention are, as indicated earlier herein, useful in olefin polymer compositions. They generally are present in such compositions in combination with a dialkyl thiodipropionate where the alkyl group is one having 10–20 carbon atoms; distearyl dithiopropionate is preferred. The acetal ester is used in concentrations ranging from about 0.01% to about 1.0%; the dialkyl thiodipropionate is used in concentrations ranging from about 0.05% to about 0.75%.

The efficacy of the acetal-esters herein as polymer stabilizers is shown by the data set out in the Table below. The data is derived from thermal stability tests carried out at 150° C. Each sample is heated at this temperature and inspected at periodic intervals until it fails (as evidenced by embrittlement, crazing and/or cracking). The samples each consist of polypropylene containing 0.10 pph (parts per hundred parts of resin), calcium stearate and other additives as shown. Color ratings (Hunter L-b) are assigned to each sample prior to (initial) and after (Final) 600 hours at 150° C.

The stability rating is measured as the number of hours required for failure, and is the average of these samples.

|  |  |  | Color | | |
| --- | --- | --- | --- | --- | --- |
| Acetal-Ester (pph) |  | DSTDP (pph) | Initial | Final | Stability |
| Product of | 0.03 | 0.25 | 75.8 | 74.0 | — |
| Example 1 | 0.05 | 0.20 | — | — | 1264 |
|  | 0.05 | 0.30 | — | — | 1368 |
|  | 0.075 | 0.25 | 75.6 | 73.9 | 1632 |
|  | 0.075 | 0.30 | — | — | 1800 |
| Product of | 0.03 | 0.25 | 75.6 | 74.0 | 1304 |
| Example 2 | 0.05 | 0.20 | — | — | 1464 |
|  | 0.05 | 0.30 | — | — | 1664 |
|  | 0.75 | 0.25 | 74.8 | 72.1 | 1632 |
|  | 0.75 | 0.35 | — | — | 1824 |
| Product of | 0.05 | 0.25 | 74.3 | — |  |
| Example 3 | 0.10 | 0.25 | 74.5 | 67.9 |  |
| Product of | 0.05 | 0.25 |  |  | 1416 |
| Example 4 |  |  |  |  |  |
| Product of | 0.05 | 0.25 | 76.1 | — |  |
| Example 5 | 0.10 | 0.25 | 74.3 | 70.8 |  |
| None | — | 0.25 |  |  | 168 |

All parts and percentages herein, unless otherwise expressly stated, are by weight.

We claim:
1. A process for the preparation of esters of pentaerythritol monoacetal comprising reacting a monoacetal of pentaerythritol having the structure

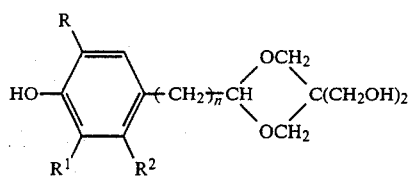

where R is alkyl, cycloalkyl or aralkyl having 3–10 carbon atoms, $R^1$ is alkyl of 1–6 carbon atoms, and $R^2$ is lower alkyl or hydrogen, with an ester-forming compound having the structure $Cl_n$—A—X where n is 1 or 2, A is

or p—O, X is an organic radical selected from the group consisting of phenolic groups, alkyl phenyl groups and phenylalkyl groups, and n is 0–3.

2. The process of claim 1 wherein R and $R^1$ are each tertiary butyl and $R^2$ is hydrogen.

3. The process of claim 1 wherein R is tertiary butyl and $R^1$ and $R^2$ are each methyl.

4. The process of claim 1 wherein A is P—O.

5. The process of claim 1 wherein A is

6. An ester of a pentaerythritol monoacetal having the structure

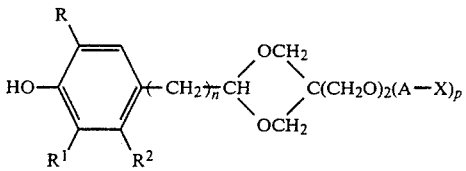

where R is alkyl, cycloalkyl or aralkyl having 3–10 carbon atoms, $R^1$ is alkyl of 1–6 carbon atoms, $R^2$ is lower alkyl or hydrogen, A is

or P—O, X is an organic radical selected from the group consisting of phenolic groups, alkyl phenyl groups and phenyl alkyl groups, n is 0–3 and p is 1–2.

7. The ester of claim 6 wherein A is

8. The ester of claim 6 wherein A is P—O.